(12) United States Patent
Abel

(10) Patent No.: US 6,428,317 B1
(45) Date of Patent: Aug. 6, 2002

(54) BARBED ENDODONTIC INSTRUMENT

(75) Inventor: Michael Abel, Signal Mountain, TN (US)

(73) Assignee: Abelity, LLC, Lookout Mountain, GA (US)

(*) Notice: Subject to any disclaimer, the term of this patent is extended or adjusted under 35 U.S.C. 154(b) by 0 days.

(21) Appl. No.: 09/652,278

(22) Filed: Aug. 30, 2000

Related U.S. Application Data

(60) Provisional application No. 60/151,416, filed on Aug. 30, 1999.

(51) Int. Cl.[7] ................................................ A61C 5/02
(52) U.S. Cl. .................................................... 433/102
(58) Field of Search ................... 433/102, 165; 29/896.1; 72/700, 324

(56) References Cited

U.S. PATENT DOCUMENTS

| | | | | |
|---|---|---|---|---|
| 251,598 A | * | 12/1881 | Johanson | 433/102 |
| 1,402,229 A | * | 1/1922 | Hauptmeyer | 433/102 |
| 4,299,571 A | | 11/1981 | McSpadden | 433/102 |
| 4,332,561 A | | 6/1982 | McSpadden | 433/102 |
| 4,353,698 A | | 10/1982 | McSpadden | 433/164 |
| 4,457,710 A | | 7/1984 | McSpadden | 433/81 |
| 4,904,185 A | | 2/1990 | McSpadden | 433/164 |
| 5,035,617 A | | 7/1991 | McSpadden | 433/102 |
| 5,104,316 A | | 4/1992 | McSpadden | 433/102 |
| 5,464,362 A | | 11/1995 | Heath et al. | 451/48 |
| 5,735,689 A | | 4/1998 | McSpadden | 433/102 |
| 5,843,244 A | | 12/1998 | Pellon et al. | 148/563 |
| 5,882,198 A | | 3/1999 | Taylor et al. | 433/102 |
| 5,902,106 A | | 5/1999 | McSpadden | 433/102 |
| 5,938,440 A | | 8/1999 | McSpadden | 433/102 |
| 5,980,250 A | | 11/1999 | McSpadden | 433/102 |

OTHER PUBLICATIONS

Walia, Harmeet, et al. "An Initial Investigation of the Bending and Torsional Properties of Nitinol Root Canal Files." *Journal of Endodontics,* vol. 14, No. 7, Jul. 1988, pp. 346–351.

* cited by examiner

*Primary Examiner*—Cary E. O'Connor
(74) *Attorney, Agent, or Firm*—Jonathan A. Barney

(57) ABSTRACT

A process for producing an endodontic instrument by selectively hacking burr-like cutting edges into a rod of a nickel-titanium alloy. Nickel-titanium being a particularly difficult material to machine; process parameters for performing said hacking procedure are disclosed herein. The cutting edges may be formed in a variety of patterns, such as helical or linear patterns, on the instrument.

14 Claims, 7 Drawing Sheets

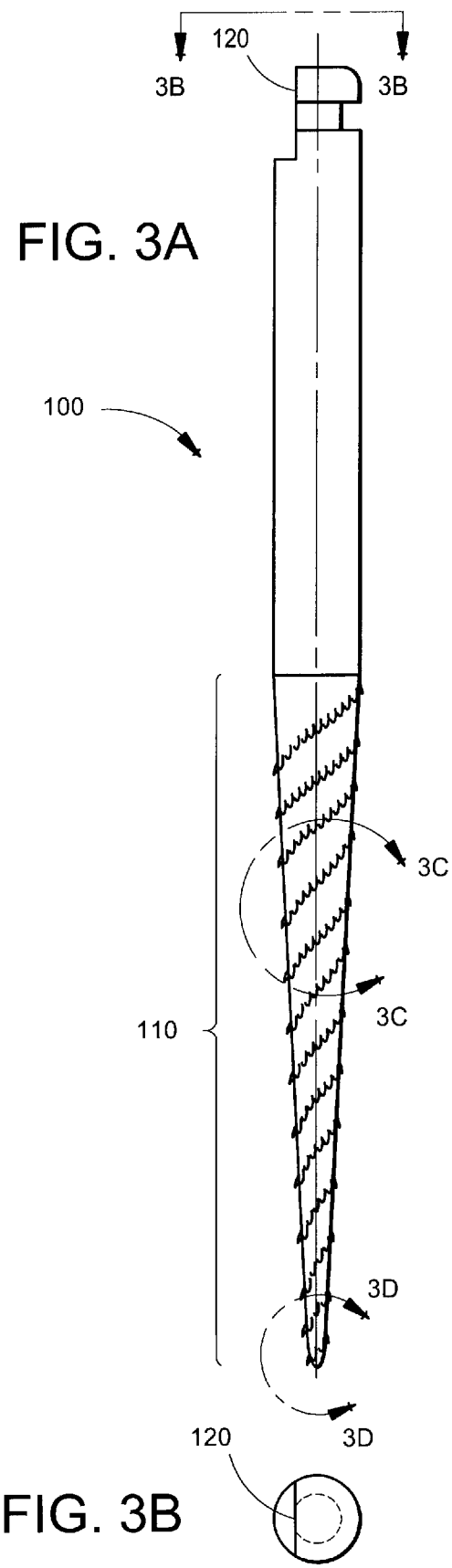
FIG. 3A
FIG. 3B
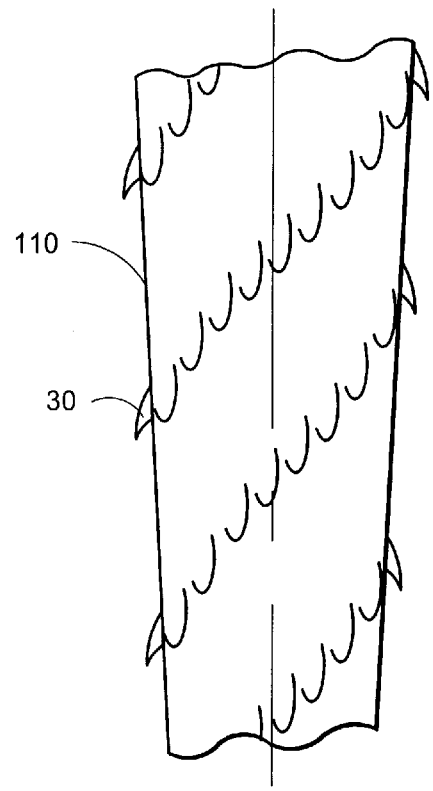
FIG. 3C
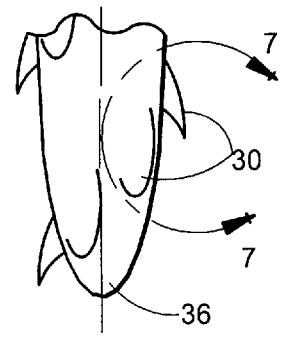
FIG. 3D

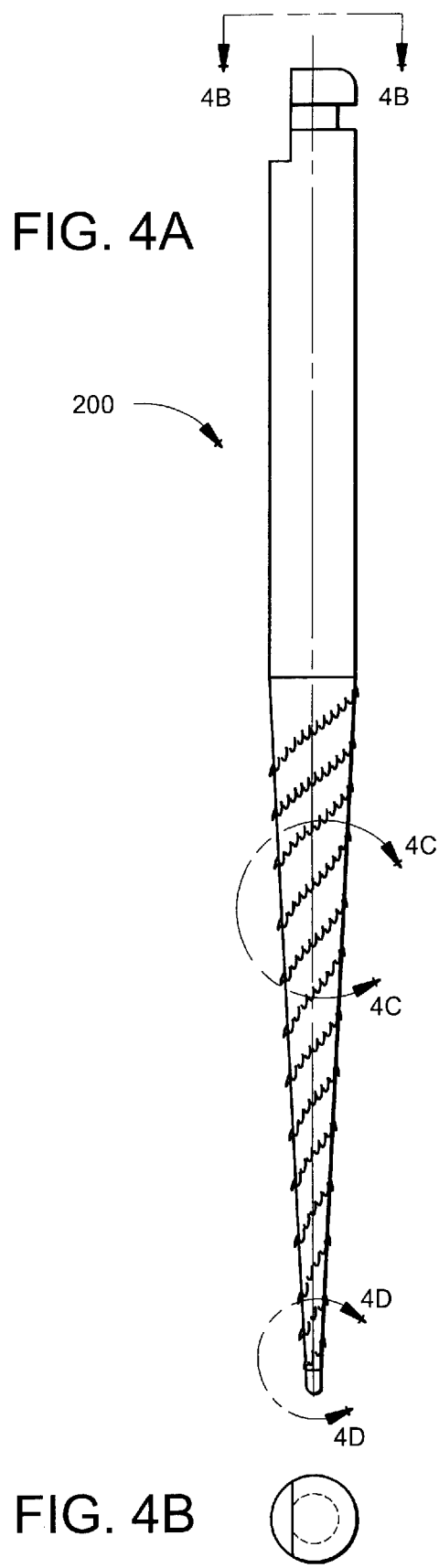
FIG. 4A
FIG. 4B
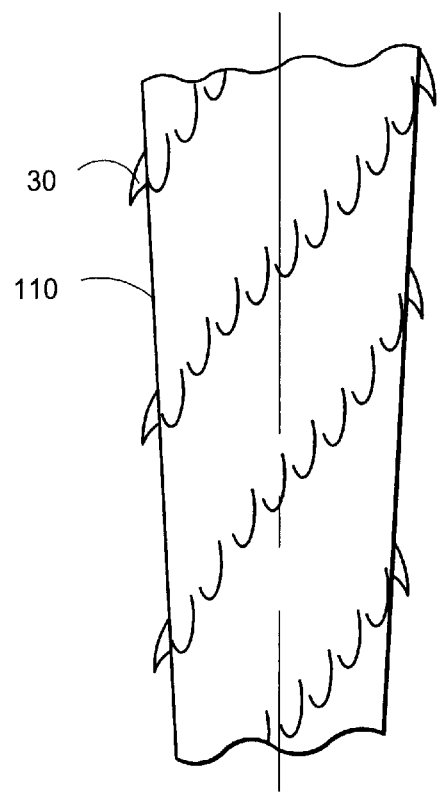
FIG. 4C
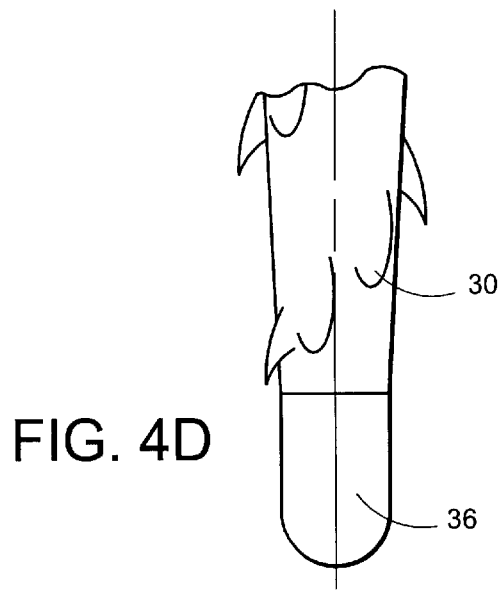
FIG. 4D

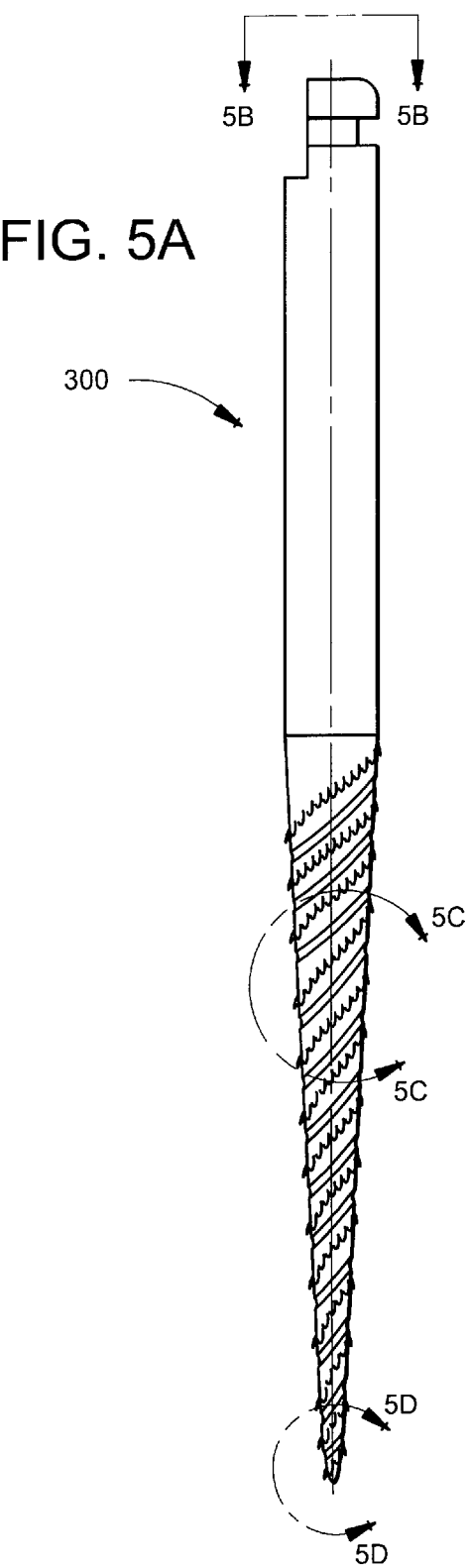
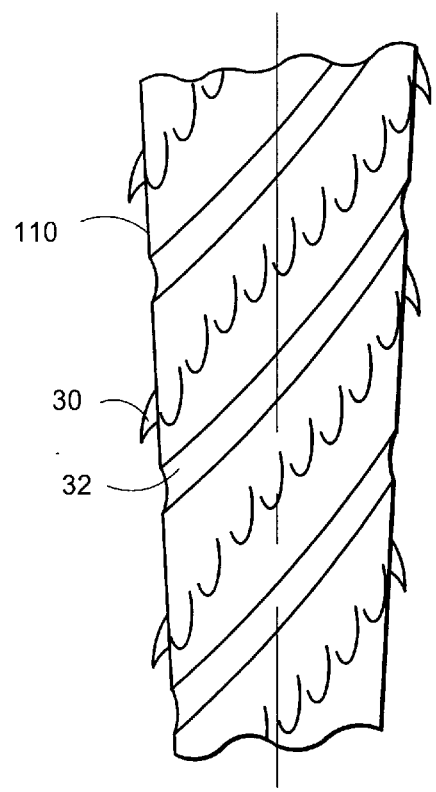
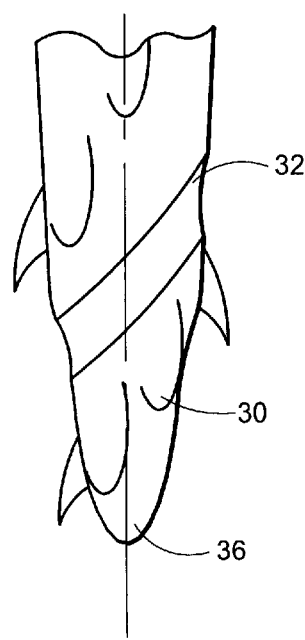
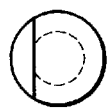
FIG. 5A
FIG. 5C
FIG. 5B
FIG. 5D

BARBED ENDODONTIC INSTRUMENT

RELATED APPLICATIONS

Applicant hereby claims priority to U.S. provisional patent application Ser. No. 60/151,416 filed Aug. 30, 1999.

BACKGROUND OF THE INVENTION

1. Field of the Invention

The invention relates generally to the field of dentistry and more particularly to endodontic instruments used to enlarge root canals.

2. Description of the Related Art

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In a root canal procedure, the dentist removes inflamed tissue and debris from the canal prior to filling the canal with an inert filling material. In performing this procedure the dentist must gain access to the entire canal, shaping it as necessary. But root canals normally are very small in diameter, and they are usually quite curved. It is therefore very difficult to gain access to the full length of a root canal.

Many tools have been designed to perform the difficult task of cleaning and shaping root canals. Historically, dentists have been required to use a multitude of tools to remove the soft and hard tissues of the root canal. These tools, usually called endodontic files, have been made by three basic processes: In one process, a file is created by twisting a prismatic rod of either square or triangular cross section in order to create a file with a fluted cutting edge. The second process involves grinding helical flutes into a circular or tapered rod to create a file with one or more helical cutting surfaces. The third method involves "hacking" or rapidly striking a circular or tapered rod with a blade at a given angle along the length of the rod, thus creating a plurality of burr-like barbs or cutting edges. Each of these methods produces an instrument having unique attributes, advantages, and disadvantages.

Endodontic files have historically been made from stainless steel, but due to the inherent stiffness of steel, these tools can pose a significant danger of breakage in the curved root canal. More recent designs have attempted to overcome the problems created by the stiffness of steel. Some attempt to alter the geometry of the stainless steel file in order to provide more flexibility. But, this approach has had only limited success, and the stainless steel tools still have a tendency to break.

A series of comparative tests of endodontic instruments made of nickel-titanium alloy (Nitinol™ or NiTi) and stainless steel were conducted and published in an article entitled "An Initial Investigation of the Bending and the Torsional Properties of Nitinol Root Canal Files," Journal of Endodontics, Volume 14, No. 7, July 1988, pages 346–351. The Nitinol instruments involved in these tests were manufactured in accordance with fabrication procedures and operating parameters conventionally used in the machining of stainless steel endodontic instruments. This process involved grinding a helical flute in a tapered shaft to form helical cutting edges.

The reported tests demonstrated that the NiTi instruments produced by the described machining process exhibited superior flexibility and torsional properties as compared to stainless steel instruments, but the cutting edges of the instruments exhibited heavily deformed metal deposits which, according to the article, rendered the instruments generally unsatisfactory for clinical use.

In general, alloys of nickel (Ni) and titanium (Ti) have a relatively low modulus of elasticity (0.83 GPa) over a wide range, a relatively high yield strength (0.195–690 MPa), and the unique and the unusual property of being "superelastic" over a limited temperature range. Superelasticity refers to the highly exaggerated elasticity, or spring-back, observed in many NiTi and other superelastic alloys over a limited temperature range. Such alloys can deliver over 15 times the elastic motion of a spring steel, i.e., withstand twisting or bending up to 15 times greater without permanent deformation. The particular physical and other properties of Nitinol alloys may be varied over a wide range by adjusting the precise Ni/Ti ratio used. However, the superelastic properties of NiTi also make the material very difficult to machine.

For these reasons, machining of NiTi tools for endodontic use has been an area of significant development efforts in recent years. For example, U.S. Pat. No. 5,464,362 to Heath et. al. describes a method of grinding a rod of a nickel-titanium alloy in order to create a fluted file. However, this process remains relatively expensive and slow.

Accordingly, there is a need for an improved production process which will allow for more economical manufacture of an endodontic tool from nickel titanium alloys and similar super-elastic materials having increased flexibility and versatility.

SUMMARY OF THE INVENTION

It is therefore an object of the present invention to provide an improved method of manufacturing instruments from nickel-titanium alloys and other similar superelastic materials. It is another object of the invention to provide an endodontic instrument having a reduced tendency to break during use. It is another object of the invention to reduce the number of instruments necessary to enlarge a root canal. Still another object of the invention is to provide an endodontic instrument which can be more quickly and economically produced.

According to one embodiment of the present invention, an endodontic file is created by cutting/hacking a shaft to form barb-like cutting edges similar to a nerve broach. The cutting edges or teeth are preferably formed in such a way that the "broach" file effectively cuts/debrides hard tissue (known in the art as dentin) as well as soft tissue, thus, forming an optimal canal shape. The cutting edges or teeth would preferably be formed at an angle to the centerline of the instrument to provide optimal cutting efficiency and material removal. A dental broach instrument having features and advantages of the present invention may be generally characterized as having multiple discrete teeth/barbs formed at an angle from the centerline of the shaft, increased flexibility due to the material and design of the broach, and significantly reduced manufacturing cost.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which:

FIGS. 3A–D are side, top, shank detail and tip detail views, respectively, of an endodontic instrument having features and advantages of the present invention having barbed cutting projections arranged in a helical pattern along the shank;

FIGS. 4A–D are side, top, shank detail and tip detail views, respectively, of an alternative embodiment of the endodontic file of FIGS. 4A–D, modified to include a non-aggressive tip;

FIGS. 5A–D are side, top, shank detail and tip detail views, respectively, of a further alternative embodiment of an endodontic file having features and advantages of the present invention including helical flutes spaced between adjacent helical patterns of barbed cutting projections;

DETAILED DESCRIPTION OF THE PREFERRED EMBODIMENT

Figure 1:
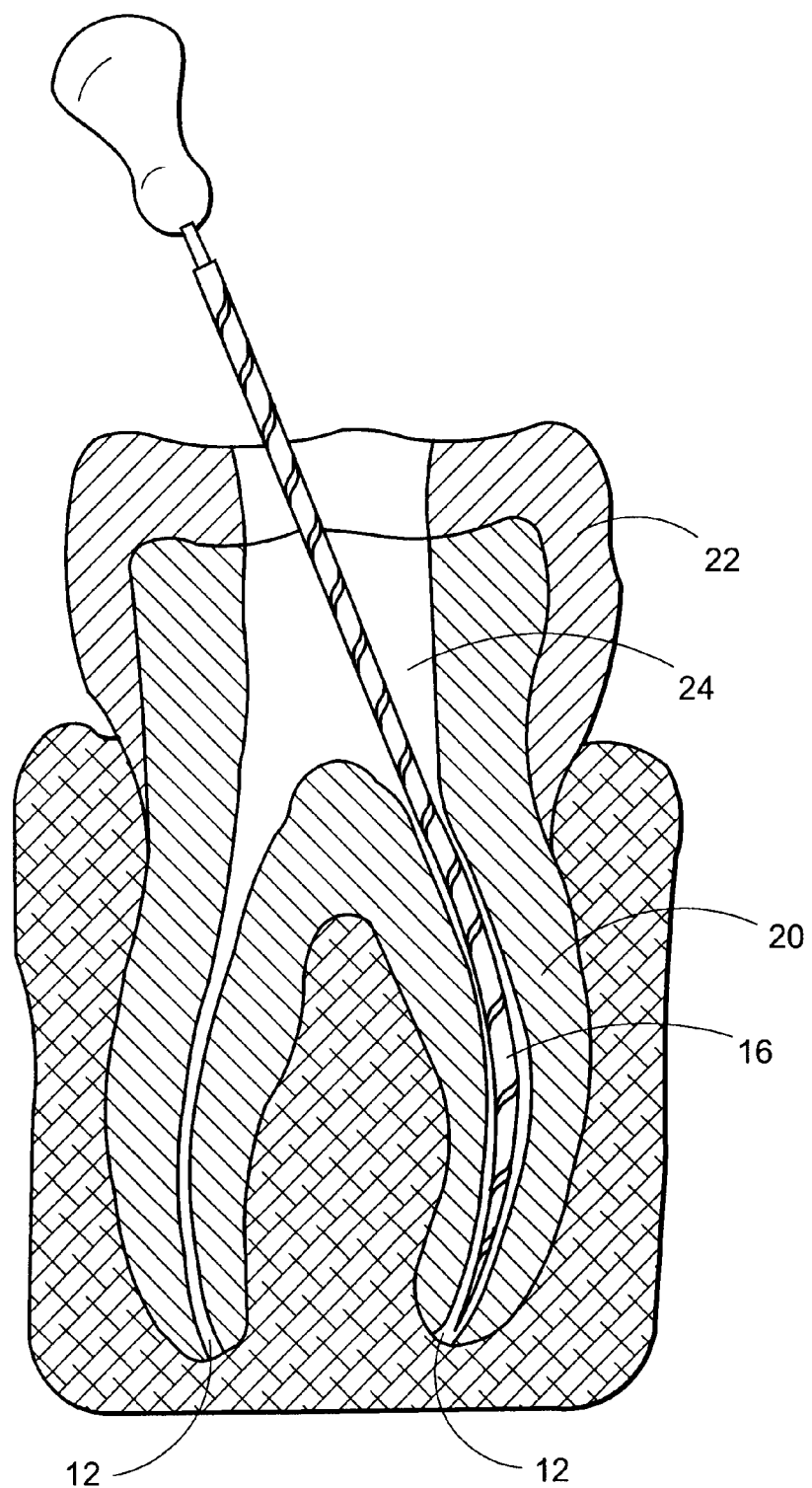
FIG. 1 is a section view of a tooth and root structure illustrating the use of an endodontic file for performing a typical root canal procedure.

FIG. 1 schematically shows an endodontic file inserted into the root canal 12 of a tooth, including the pulp tissue 24 and dentin 20 to be removed from the root canal 12. The endodontic file 16 is inserted through a hole formed in the crown 22 of the tooth, and into the root canal 12. It may be rotated there within, or it may be moved inward and outward in a reciprocating motion, or a combination thereof, as desired.

All of the endodontic files illustrated and described herein are preferably formed from a select alloy of titanium and nickel (Ni—Ti)—commonly known as "NiTi" Nitinol™.

Such materials may be obtained from any one of a number of supplier/fabricators well known in the specialty metals supply industry. Useful alloys with 49.0 to 50.7 atomic % of Ti are commercially available, but alloys in the range of 49.0 to 49.4% Ti are most preferred for purposes of practicing the present invention. Special annealing processes, heat treatments and/or the addition of trace elements, such as oxygen (O), nitrogen (N), iron (Fe), aluminum (Al), chromium (Cr), cobalt (Co) vanadium (V), zirconium (Zr) and copper (Cu), can also have very significant effects on desired superelastic properties and performance of the materials. See, for example, U.S. Pat. No. 5,843,244 to Pelton, incorporated herein by reference.

Of course, the invention disclosed herein is not limited specifically to Ni—Ti alloys, but may be practiced using any one of a number of other suitable alloy materials having the desired superelastic properties, such as Silver-Cadmium (Ag—Cd), Gold-Cadmium (Au—Cd) and Iron-Platinum (Fe3Pt), to name but a few. In the preferred embodiment a NiTi alloy comprising about 51% Nickel and 49% Titanium was selected. Drawn wire stock formed from such alloys may be obtained in various diameters, for example, from Memry Corporation under the specified alloy name "Nitinol BA".

TABLES 1–4 below list certain selected properties of NiTi alloys having preferred application to the present invention:

TABLE 1

| MECHANICAL PROPERTIES | |
|---|---|
| Young's Modulus | |
| austenite | ~83 GPa (12 × $10^6$ psi) |
| martensite | ~28 to 41 GPa (~4 × $10^6$ to 6 × $10^6$ psi) |
| Yield Strength | |
| austenite | 196 to 690 MPa (28 to 100 ksi) |
| martensite | 70 to 140 MPa (10 to 20 ksi) |
| Ultimate Tensile Strength | |
| fully annealed | 895 MPa (130 ksi) |
| work hardened | 1900 MPa (275 ksi) |
| Poisson's Ratio | 0.33 |
| Elongation at Failure | |
| fully annealed | 25 to 50% |
| work hardened | 5 to 10% |

TABLE 2

| Physical Properties | |
|---|---|
| Melting Point | 1300° C. (2370° F.) |
| Density | 6.45 g/cm$^3$ (0.233 lb/in$^3$) |
| Thermal Conductivity | |
| austenite | 0.18 W/cm · ° C. (10.4 BTU/ft · hr · ° F.) |
| martensite | 0.086 W/cm · ° C. (5.0 BTU/ft · hr · ° F.) |
| Coeff. of Therm. Expansion | |
| austenite | 11.0 × $10^{-6}$/° C. (6.11 × $10^{-6}$/° F.) |
| martensite | 6.6 × $10^{-6}$/° C. (3.67 × $10^{-6}$/° F.) |
| Specific Heat | 0.20 cal/g · ° C. (0.20 BTU/lb · ° F.) |
| Corrosion Performance | excellent |

TABLE 3

Transformation Properties

| | |
|---|---|
| Transformation Temperature | −200 to +110° C. |
| Latent Heat of Transformation | 5.78 cal/g |
| Transformation Strain (for polycrystalline material) | |
| for 1 cycle | max 8% |
| for 100 cycles | 6% |
| for 100,000 cycles | 4% |
| Hysteresis | 30 to 50° C. |

Nickel-titanium has several peculiar properties that make it very useful in this and other applications. In particular, the alloy has the unusual ability to reversibly change its crystalline structure from a hard, high-modulus "austentitic" crystalline form to a soft, ductile "martensitic" crystalline form upon application of pressure and/or by cooling. This results in a highly elastic material having a very pronounced pseudo-elastic strain characteristic. This pseudo-elastic elastic strain characteristic is often described as "superelasticity."

As a result of this fully reversible stress-induced crystalline transformation process a very tough and rubber-like elasticity ("superelasticity") is provided in such alloys. These material properties are very desirable for the present application. However, they also make such alloys very difficult to machine using conventional machining techniques. Grinding is the presently accepted method for machining NiTi alloys, but even then, special procedures and parameters must typically be observed to obtain reliable results. See, for example, U.S. Pat. No. 5,464,362 to Heath et. al., which describes a method of grinding a rod of a Nickel-titanium alloy in order to create a fluted endodontic file. The cost of purchasing and operating the specialized grinding machines and grinding wheels required, and the relatively slow grinding process make the endodontic files produced by this method very expensive.

One relatively low cost method that is known for forming an endodontic file from a stainless steel rod includes the principle step of "hacking" or rapidly striking the rod with a blade at a given angle, thus creating a plurality of burr-like barbs or cutting edges along the length of the rod. However, this method has never, to the knowledge of the inventor, been successfully applied to form highly-flexible endodontic files produced, for example, from rods of nickel-titanium alloy or similar superelastic materials.

The process of hacking burr-like cutting edges in nickel-titanium rods is very difficult and quite unreliable as compared to the process of creating the same bur-like cutting projections in rods of stainless steel material. When a blade impinges on a nickel-titanium rod under the same circumstances as those presently used for stainless rods, a stress-induced martensitic crystalline transformation occurs at the point of contact, which virtually instantaneously transforms the material into a soft, highly resilient and tough material. This inhibits further penetration of the blade and any significant permanent deformation of the material.

Thus, presently known hacking methods and machines are ineffective to reliably form the desired cutting projections on a nickel-titanium rod. However, through an iterative process of experimentation, it was discovered that the machine and/or operating parameters could be inexpensively reconfigured and modified as described in detail herein to reliably produce barbed cutting projections along the length of a nickel-titanium rod to form a low-cost, more effective endodontic root canal file.

Figure 2A:
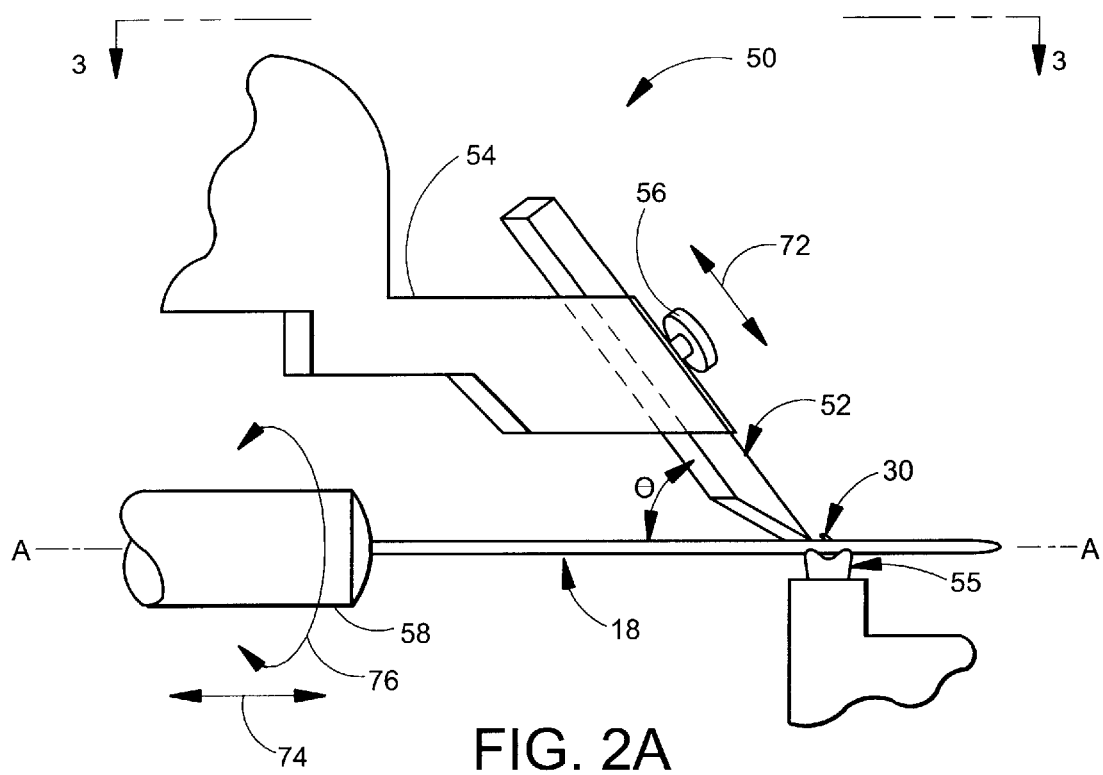
FIG. 2A is a partial schematic representation of a machine used to produce an endodontic instrument having features and advantages of the present invention, the machine being viewed from one side.
Figure 2B:
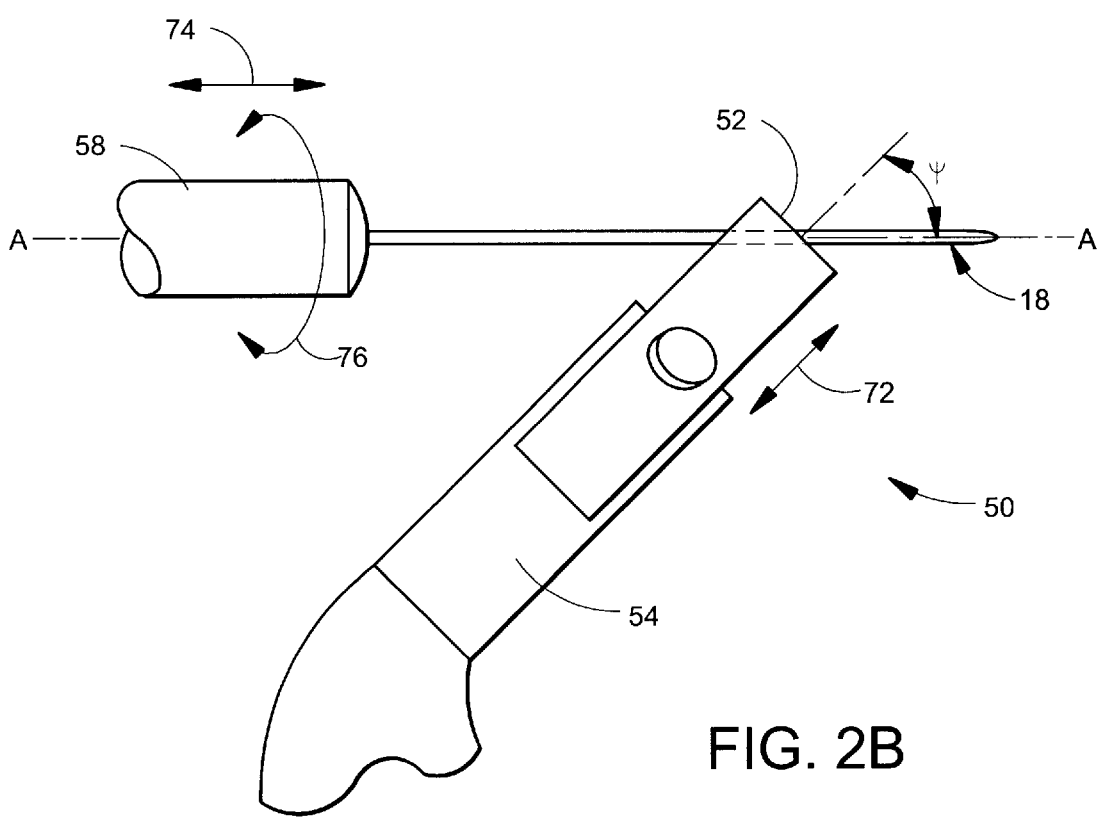
FIG. 2B is a top view of the machine of FIG. 2A.
Figure 6A:
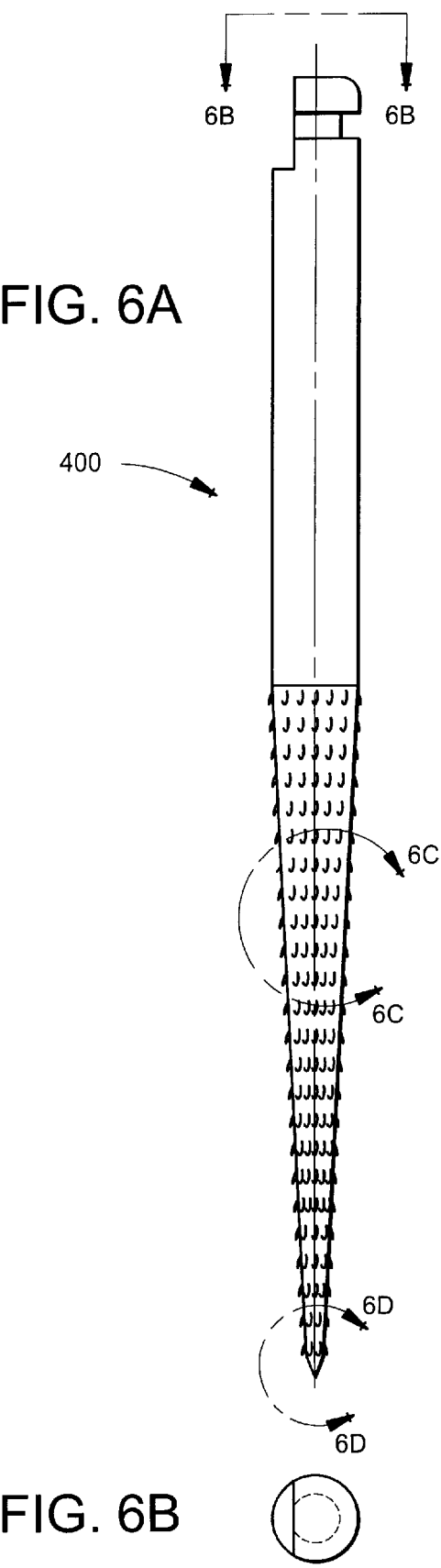
FIGS. 6A–D are side, top, shank detail and tip detail views, respectively, of a further alternative embodiment of an endodontic file having features and advantages of the present invention including barbed cutting projections arranged in a linear or axial pattern along a hollow, tubular shaft.
Figure 6B:
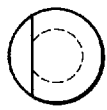
Figure 6C:
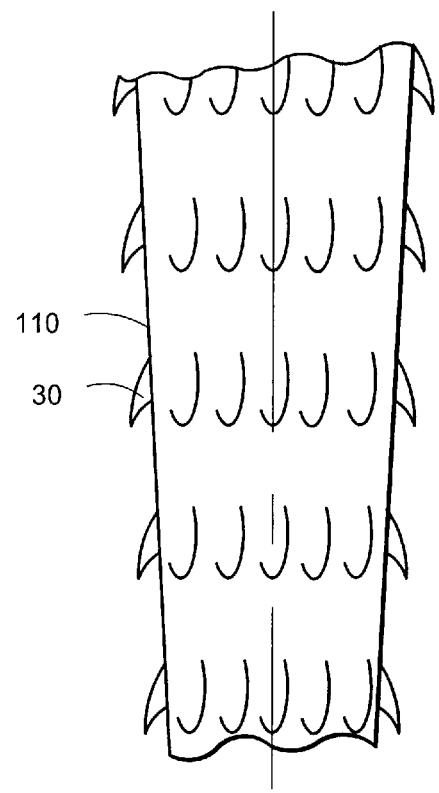
Figure 6D:
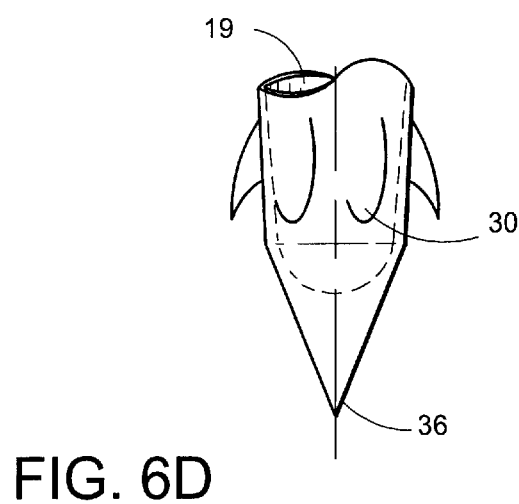

FIGS. 2A and 2B schematically illustrate the fundamental operation of a barb-forming machine used to produce an endodontic file having features and advantages of the present invention. The barb-forming machine 50 preferably includes at least one blade 52 held by a movable arm 54, and secured via a set screw 56. The motion of the arm is preferably controlled by various cams and linkages (not shown) which are arranged and adapted to supply the necessary motion 72 relative to the work piece 18 and other process parameters as described herein. Another portion of the machine preferably also comprises a chuck 58 in which a rod 18 of nickel-titanium alloy or similar material may be fixed during machining. The chuck is preferably mounted to a portion of the machine (not shown) capable of rotating (as indicated by arrow 76) and translating (as indicated by arrow 74) the chuck 58 and rod 18 about and along axis A-A, also termed the longitudinal axis. A support bearing 55 or similar support surface is preferably disposed under the rod 18 at the point of contact between the rod and the hacking blade 52.

The basic construction and operating principles of such hacking machines are known in the art. The present invention derives from the application of the modified machine 50 and machining process to form barbed endodontic instruments from rods of nickel-titanium alloy or similar superelastic materials. The present invention also resides in the modification of the hacking machine and the discovery of particular machine settings and operating parameters for achieving reliable formation of barbed cutting edges 30 in nickel-titanium and similar resilient alloys using the machine 50 or a similarly constructed machine.

In a preferred embodiment, the arm 54 is mounted such that the blade 52 impinges on the rod 18 at a rake angle θ—preferably between about 3–10° and most preferably about 5°—relative to a vertical plane through the longitudinal axis A-A (FIG. 2A). Simultaneously, a relatively large downward force of greater than about 2–5 pounds and most preferably greater than about 20–30 pounds is applied to urge the blade 52 against the rod 18. When the blade 52 strikes the rod 18 according to conditions of the present invention, a small burr-like cutting edge 30 or cutting projection 33 (shown in greater detail in FIGS. 8 and 9) is reliably formed on the rod 18. By translating and/or rotating the rod 18 held in the chuck 58, a plurality of such cutting edges 30 can be formed along the length and/or around the circumference of the rod 18. If desired, the cutting blade can be canted by an angle ψ—preferably between about 10–45° and most preferably about 20°—relative a horizontal plane through the longitudinal axis A—A (FIG. 2B).

Figure 7:
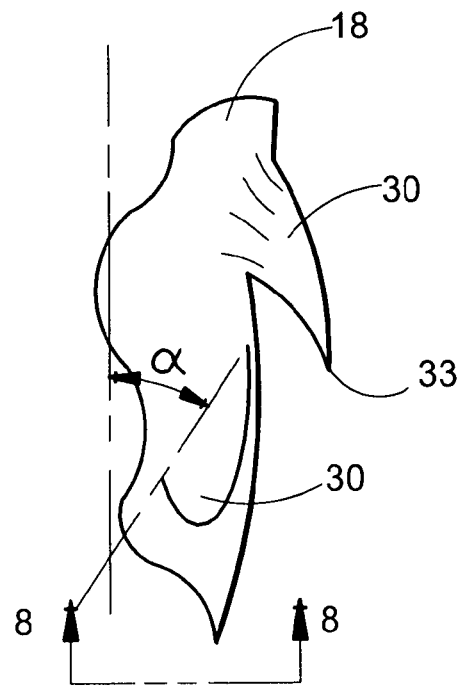
FIG. 7 is a side detail cutaway view of a barbed cutting projection having features and advantages of the present invention.
Figure 8:
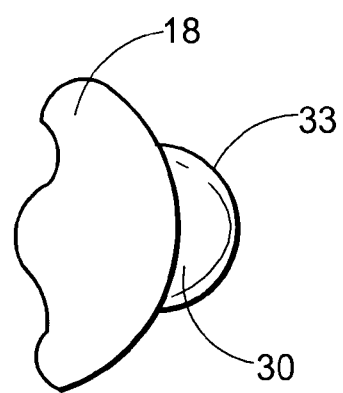
FIG. 8 is a top detail cutaway view of the barbed cutting projection of FIG. 8.

As will be recognized by those skilled in the art, different combinations of translational and rotational movements, rake angles and canting angles, will produce cutting edges 30 along the rod having various patterns and characteristics. The size of each cutting projection 33 can also be varied by adjusting the force applied by the cutting blade 52 against the rod 18 and/or the stroke of the cutting blade 52. FIG. 7 is a side detail cutaway view of a barbed cutting projection being formed in accordance with the machining process described above and having features and advantages of the present invention. FIG. 8 is a top detail cutaway view of the barbed cutting projection of FIG. 7, illustrating the general shape and structure thereof.

A nickel-titanium endodontic instrument 100 having a helical pattern of cutting projections formed along its working length 110 is illustrated in FIGS. 3A–D. The cutting projections may be produced by the machining/hacking process described above, including the steps of rotating and translating the rod 18 between successive blade strikes. The instrument 100 preferably includes a proximal end having a D-shaped chuck-engaging portion 120 for fitting to the chuck of a standard dental hand piece or other manipulating device, as desired.

FIGS. 4A–D illustrate a nickel-titanium endodontic instrument 200 having a helical pattern of cutting projections formed along its length, as illustrated and described above in connection with FIGS. 3A–D. The instrument 200 is modified in that the distal tip 36 is rounded, generally providing a non-aggressive tip or non-cutting tip. In practice, a wide variety of tip designs, both cutting and non-cutting, may be used while enjoying the benefits and advantages of the present invention.

FIGS. 5A–D illustrate a nickel-titanium endodontic instrument 300 having a helical pattern of cutting projections formed along its length, as illustrated and described above in connection with FIGS. 3A–D. The instrument 200 is modified in that it preferably includes flutes 32 machined into the rod 18 as well as hacked burr-like cutting edges 30. The flutes help remove and lift out debris produced during use in a root canal procedure. In practice, a wide variety of combination of flutes and barbs may be used while enjoying the benefits and advantages of the present invention.

FIGS. 6A–D illustrate a nickel-titanium endodontic instrument 400 having a linear pattern of cutting projections formed along its length. The cutting projections may be produced by the machining/hacking process described above, including the steps of translating the rod 18 between successive strikes, while preventing rotation thereof. The instrument 400 is also modified in that it is formed from a hollow tube of nickel-titanium alloy. The hollow tube allows for use of a cooling fluid for improved lubrication and chip removal. Preferably a piece of wire or other solid material shaped to fit within the tube 19 would be inserted into the tube 19 during the hacking process so as to provide support. The wire would then be removed after processing, leaving a hollow endodontic instrument 400.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method of fabricating an endodontic instrument comprising:

providing a rod of a superelastic alloy;

the step of hacking said rod to form barb-like cutting edges thereon;

a blade striking said rod at an angle of about 5° in the vertical plane;

said blade impinging on said rod with 20–30 lbs of force.

2. The method of claim 1 wherein said rod is tapered.

3. The method of claim 2 wherein the size of each of said cutting edges is directly proportional to the diameter of said rod at the point of each of said cutting edges.

4. The endodontic instrument made by the method of claim 1 wherein said barb-like cutting edges are formed at an angle to the centerline of said rod.

5. The method of claim 1 wherein said rod is a hollow tube of a superelastic alloy.

6. The method of claim 1:

wherein said rod is a hollow tube of a superelastic alloy; and further comprising the steps of:

placing a solid rod or wire inside the hollow space of said tube before said hacking procedure;

removing said rod or wire from within said tube after said hacking procedure.

7. The method of claim 1 wherein said cutting edges are formed at an angle relative to the longitudinal axis of said rod.

8. The method of claim 1 wherein said cutting edges are formed in a substantially helical pattern about said rod.

9. The method of claim 1 wherein said cutting edges are formed in a substantially linear pattern, said pattern being substantially parallel to the longitudinal axis of said rod.

10. The endodontic instrument of claim 9 further comprising flutes formed thereon.

11. An endodontic instrument comprising:

a rod of a superelastic alloy material;

barb-like cutting edges formed by selectively hacking said rod with a blade striking said rod at an angle of 5° degrees, and with 20–30 lbs of force.

12. The endodontic instrument of claim 11 wherein said superelastic alloy is a nickel-titanium alloy comprising 51% Nickel and 49% Titanium.

13. The endodontic instrument of claim 11 wherein said barb-like cutting edges are formed at an angle to the centerline of said rod.

14. A method of forming an endodontic instrument comprising:

providing a tapered rod of a superelastic alloy;

the step of hacking said rod to form barb-like cutting edges thereon;

a blade striking said rod at an angle of 5° in the vertical plane;

said blade impinging on said rod with 20–30 lbs of force; and said cutting edges being formed at an angle between 10° and 45° relative to the central axis of said rod.

* * * * *